United States Patent
Duebendorfer et al.

(10) Patent No.: US 6,538,735 B1
(45) Date of Patent: Mar. 25, 2003

(54) METHOD AND APPARATUS FOR PRODUCING AND MEASURING LIGHT AND FOR DETERMINING THE AMOUNTS OF ANALYTES IN MICROPLATE WELLS

(75) Inventors: Juerg Duebendorfer, Wheaton, IL (US); Donald Jones, Lisle, IL (US); Kenneth Neumann, Naperville, IL (US); Chang Jin Wang, East Lyme, CT (US)

(73) Assignee: Packard Instrument Company, Downers Grove, IL (US)

( * ) Notice: Subject to any disclaimer, the term of this patent is extended or adjusted under 35 U.S.C. 154(b) by 0 days.

(21) Appl. No.: 09/512,707

(22) Filed: Feb. 25, 2000

(51) Int. Cl.⁷ .................................................. G01J 3/30
(52) U.S. Cl. ...................................... 356/318; 356/317
(58) Field of Search ................................. 356/417, 318, 356/317, 244, 246, 73; 250/458.1, 227.22; 385/12, 13, 115, 117, 118

(56) References Cited

U.S. PATENT DOCUMENTS

| | | | |
|---|---|---|---|
| 4,626,684 A | 12/1986 | Landa | 250/328 |
| 5,239,180 A * | 8/1993 | Clarke | 250/339 |
| 5,343,045 A * | 8/1994 | Gupta | 250/339.1 |
| RE34,782 E * | 11/1994 | Dandliker et al. | 250/458 |
| 5,557,415 A | 9/1996 | Nielsen et al. | 356/417 |
| 5,589,351 A | 12/1996 | Harootunian | |
| 5,682,244 A | 10/1997 | Barlow et al. | |
| 5,736,410 A * | 4/1998 | Zarling et al. | 436/172 |
| 5,919,707 A | 7/1999 | Banks et al. | |
| 5,920,399 A | 7/1999 | Sandison et al. | |
| 5,926,270 A | 7/1999 | Longacre | |
| 6,097,025 A * | 8/2000 | Modlin et al. | 250/227.22 |

FOREIGN PATENT DOCUMENTS

| | | | | |
|---|---|---|---|---|
| EP | 0 421 156 A2 | 4/1991 | | G01N/21/64 |
| WO | WO 93 13423 | 7/1993 | | G01N/35/02 |
| WO | WO 97 11354 | 3/1997 | | G01N/21/64 |
| WO | WO 98 52047 | 11/1998 | | G01N/35/00 |

* cited by examiner

*Primary Examiner*—Frank G. Font
*Assistant Examiner*—Layla Lauchman
(74) *Attorney, Agent, or Firm*—Jenkens & Gilchrist

(57) ABSTRACT

An apparatus for measuring light in samples using a high intensity light source, is presented. The system utilizes bifurcated fiber bundles to transmit light at the excitation and emission wavelength bands. It also uses a band-pass filter for eliminating extraneous light, including that which corresponds to the excitation wavelength range, while permitting the emitted light to pass to a detector for quantitation. The system employs a shutter to shield the detector while the laser light source is activated, and a controller to intermittently activate the laser light and close the shutter. The apparatus preferably includes lenses for better illumination and read out conditions. The apparatus is employed in Luminescence Oxygen Channeling Immunoassays. The method has high sensitivity, accuracy and precision, and the apparatus is highly compact. Accordingly, the analyzer can perform assays in nanoliter to microliter sample volumes in standard microplates having at least 96, 384 or 1536 wells.

62 Claims, 5 Drawing Sheets

METHOD AND APPARATUS FOR PRODUCING AND MEASURING LIGHT AND FOR DETERMINING THE AMOUNTS OF ANALYTES IN MICROPLATE WELLS

BACKGROUND OF THE INVENTION

This invention relates generally to the measurement of light created by the absorption of high intensity light of one wavelength range and subsequent re-emission at another wavelength range, and specifically to an apparatus designed to conduct bioanalytical assays by measurement of the emitted light.

Bioanalytical binding assays are widely employed by the pharmaceutical, drug-discovery and biotechnology industries. A variety of such binding assays have been developed, including but not limited to, receptor binding, enzyme activity and inhibition, protein-protein interactions, and nucleic acid hybridization. The specific techniques used to perform these assays can be generally classified as heterogeneous or homogenous.

Heterogeneous assays involve the physical separation of reacted and unreacted species prior to sample analysis. The separation is usually effected by preferential adsorption of assay components onto a suitable solid support, followed by washing of that support. A related technique involves filtration of the assay mixture through an appropriate trapping medium. These separation techniques typically result in decreased assay accuracy, decreased assay precision and an increase in labor requirements, all due to the addition of a separation step.

Homogeneous assays involve the analysis of assay mixtures without the physical separation of reacted and unreacted species. Since homogeneous assays have fewer steps, the assay accuracy and precision are higher than their heterogeneous counterparts. Moreover, labor costs are reduced. However, homogeneous assays suffer from inherent interference problems. The interference occurs as a result of the simultaneous measurement of both reacted and unreacted species. Other potential interference problems include those caused by biological matrix effects and extraneous light production from system components. These interference problems may significantly reduce the usable dynamic range, accuracy, and precision of any assay.

Both heterogeneous and homogeneous assays can use a variety of labeling and detection technologies, including but not limited to, radioisotopic, fluorometric, luminometric, and colorimetric methods. The use of these technologies is well documented in the technical literature and well known to those skilled in the art. These technologies suffer from certain limitations and disadvantages, including poor sensitivity, poor dynamic range, occupational safety risks, signal instability, and high cost.

U.S. Pat. No. 5,340,716 (Ullman, et. al. "Assay Method Utilizing Photoactivated Chemiluminescent Label") describes an alternative assay technology that possesses many of the advantages of a homogeneous system, while eliminating many of the interferences associated with traditional photon measurement technologies. The Ullman et al. patent describes the use of Luminescence Oxygen Channeling Immunoassay ("LOCI") procedures for conducting a variety of clinically important assays. Luminescent Oxygen Channeling Immunoassays can be used for quantitative determination of a variety of analytes in a wide range of concentrations. Such analytes include unbound drugs, DNA and immunoglobulins. The methods for carrying out these immunoassays have also been described in various technical publications. See, e.g., Edwin F. Ullman et al., "Luminescent Oxygen Channeling Immunoassay (LOCI™): sensitive, broadly applicable homogeneous immunoassay method"; Clinical Chemistry 42:9, pp. 1518–1526 (1996); Edwin Ullman, "Luminescent Oxygen Channeling Immunoassay (LOCI) for Human Thyroid Stimulating Hormone", in "Bioluminescence and Chemiluminescence, Proceedings of the 8th International Symposium on Bioluminescence and Chemiluminescence", Cambridge, September, 1994 (John Wiley & Sons). In the clinical laboratory, these assays are typically conducted in test tubes at sample volumes approaching 1 mL.

The pharmaceutical, drug-discovery and biotechnology industries, along with bioanalytical instrumentation vendors, have established the microplate as the preferred format in which to perform assays. This device is a plastic plate containing multiple wells in a regular array, each of which may contain a unique sample. The current standard is the 96-well plate, and assays are typically conducted in an approximate volume of 200 uL per well. As both reagent costs and sample throughput requirements increase, there is a need for an assay technology and measurement apparatus which have good precision and accuracy, high sensitivity, and can be converted to lower volume formats such as those used in 384-well and 1536-well microplates. There is also an existing need for integrated assay reaction and reading analyzers capable of operation in the nanoliter to microliter volume range.

Thus, one object of the present invention is to provide a compact apparatus that can be used in conjunction with an accurate method for producing and detecting light in liquid samples in microplate wells.

Another object of the present invention is to provide an apparatus for conducting extremely sensitive assays in very small sample volumes in high well density microplate formats.

Another object of the present invention is to provide a compact apparatus for producing and detecting light generated by biological samples using the LOCI technique, wherein the amount of light is proportional to the quantity of analyte present in the sample.

A further object of the present invention is to provide a compact apparatus for conducting bioanalytical assays using the LOCI technique by excitation of the liquid sample contained in an opaque well.

Another object of the present invention is to provide an apparatus for conducting bioanalytical assays using the LOCI technique for samples in the microliter to nanoliter volume range.

Yet another object of the present invention is to provide an apparatus for conducting bioanalytical assays using the LOCI technique in an automated fashion using microplates with 96, 384, or 1536 wells, or a labchip consisting of multiple channels.

A further object of the present invention is to provide an apparatus for conducting the aforementioned assays at a high speed by simultaneously measuring multiple wells on the microplate or channels on the labchip.

SUMMARY OF THE INVENTION

In accordance with one aspect of the present invention, a system for measuring light emitted by a sample in a microplate well, is presented. This invention includes a light source, which produces light at a first wavelength band (the excitation wavelength band), a bifurcated fiber bundle which transmits the excitation light to the sample and the emitted light to the detector, a lens which directs the excitation light into the sample and collects the light emanating from the sample at a second wavelength band (the emission wavelength band), optionally, an emission band-pass filter which blocks extraneous light, including that which corresponds to the excitation wavelength band, while passing light in the emission wavelength band, a shutter which protects the detector, thus allowing the introduction of more excitation light into the sample, and a light detector.

Unlike traditional systems of this general type, the excitation wavelength band is at a longer wavelength, and the emission wavelength band is at a shorter wavelength. Moreover, the light emanating from the sample is collected after the excitation light source is turned off. These characteristics result in lower non-specific light production, thus enhancing the sensitivity of the system.

As a result of the use of fiber bundles which transmit light to and from the sample, the light source and detector may be placed remotely to the sample. This further permits the use of multiple sets of light sources and detectors, which provides a means for simultaneously quantifying samples in different wells, thus increasing throughput.

In accordance with another aspect of the present invention, a method for measuring light emanating from a sample, produced by excitation from a high intensity light source, is presented. This invention utilizes a system for the production of high intensity light at the excitation wavelength band, which passes the high intensity light through a fiber bundle into a sample in a microplate well. The light is emitted by the liquid subjected to the excitation light as the result of the presence of materials, such as a chemiluminescent material, through the fiber bundle and is directed through an emission band-pass filter that eliminates any extraneous light, including that which corresponds to the excitation wavelength band. The light is then passed through a shutter and to a light detector, such as a photomultiplier tube. A controller intermittently activates a light source to produce high intensity light and closes a shutter whenever the high intensity light is passed through the system. This controller could be a mechanical or electronic shutter or a light source gating circuit.

In accordance with a further aspect of the present invention, an analyzer for carrying out Luminescence Oxygen Channeling Immunoassays in microplates, is presented. A biological binding reaction is carried out in liquid samples in microplate wells. A high intensity light is introduced into the well. The light initiates a photochemical reaction that results in production of light of a different wavelength. The intensity of this light is proportional to the amount of the analyte present in the sample. The emitted light resulting from the photochemical reaction has a wavelength band which is shorter than the excitation wavelength band. The emitted light is collected by a lens and a fiber bundle located above the sample, and is then passed through a filter, which eliminates extraneous light, including that which corresponds to the excitation wavelength band. The light transmitted through the filter passes through an aperture in the shutter and is measured by a detector, such as a photomultiplier tube. A controller activates the light source and closes the shutter whenever the light source is activated.

DETAILED DESCRIPTION OF THE INVENTION

Figure 1:
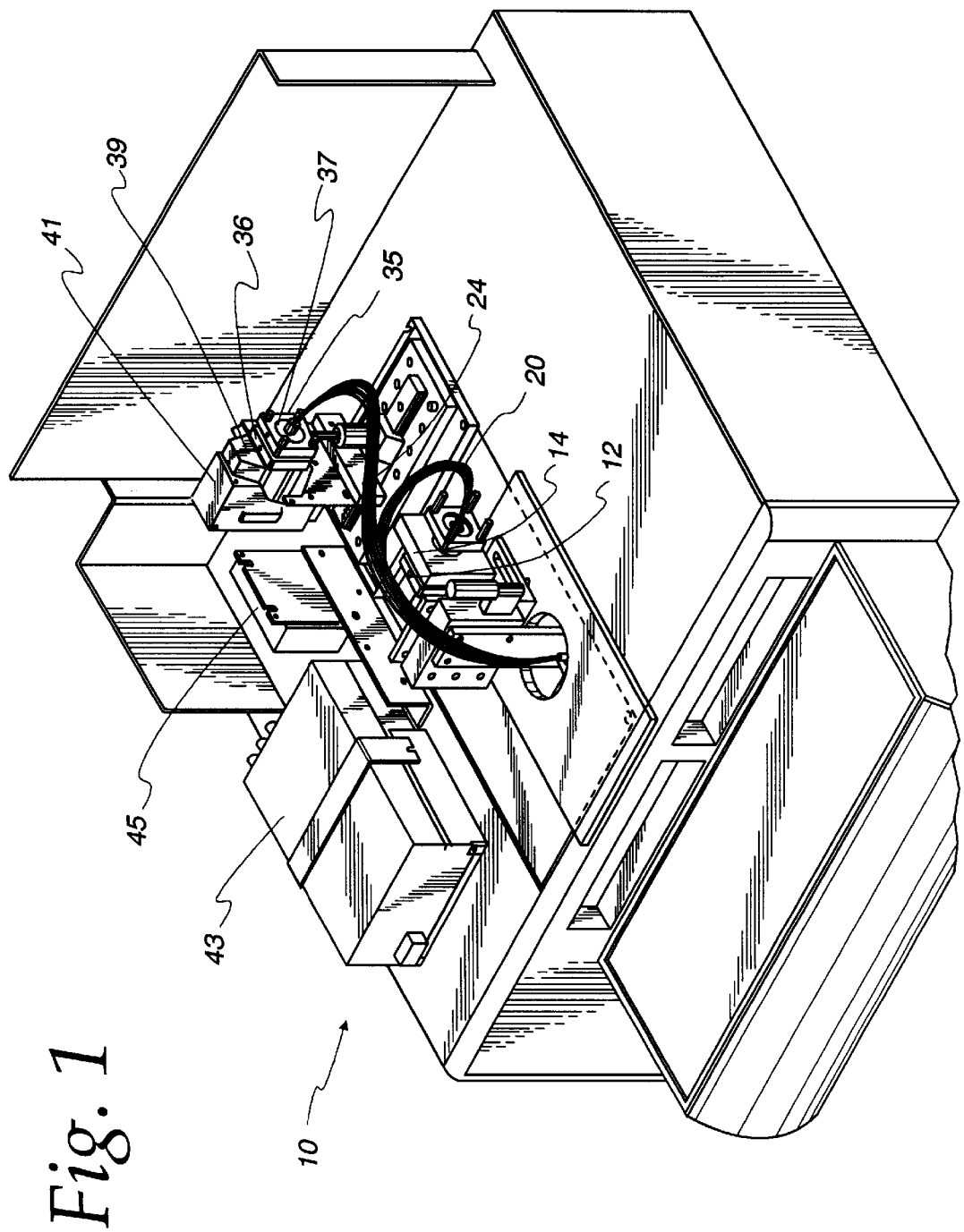
FIG. 1 is a perspective view of one embodiment of the apparatus constructed in accordance with the present invention.

It has been discovered that light can be measured with excellent sensitivity, accuracy and precision in small (i.e., nanoliter to microliter) sample volumes in wells of microplates, or from lab chips (lab-on-a-chip) using a compact apparatus that is optimized to read microplates having at least 96, 384 or 1536 wells per microplate. The sample is illuminated by high intensity light produced by a light source such as, but not limited to, a laser light source, in particular a compact laser diode. The light transmitted via a fiber bundle excites the sample, which converts the excitation light into emission light upon biomolecular binding occurrence. The emitted light is transmitted via a fiber bundle to a detector, such as, but not limited to, a photomultiplier tube, which detects and measures the amount of light after excitation ceases. The fiber bundles that transmit light at the excitation and emission wavelength bands are combined such that the common end of the bundle directly above the well includes both fiber types. The use of high intensity light results in extraordinary assay sensitivity, accuracy and precision. The system utilizes a shutter to shield the detector from this high intensity light during sample excitation. The system can also include a band-pass filter on the emission side, which eliminates extraneous light, including light corresponding to the excitation wavelength band. It has also been discovered that the system of the present invention can be used in assays based on the LOCI technique. The amount of light produced by the sample is proportional to the concentration of an analyte in the sample and the excitation wavelength is between 670 to 690 nm. The light can be efficiently generated by employing a high-intensity laser as the excitation source, emitting in the preferred wavelength region. The light emitted from the LOCI sample has a wavelength band between about 520 nm and 620 nm. This range is at a shorter wavelength than that of the excitation wavelength band. The high-intensity light is prohibited from entering the light detector by means of a shutter, which is closed while the light source is active. After the excitation source is turned off, the shutter is opened, and this allows the light indicative of the analyte to enter the detector. It has been further discovered that, in most applications, the light detector can be protected by either a mechanical, electronic or optical shutter, photomultiplier tube-gating device or by interference filters having high out-band blocking properties. The shutter prevents light from entering the detector while the laser diode is active, the filter prevents light outside the emitted wavelength band from entering the detector. The preferred detector is a standard photomultiplier tube.

A laser diode must emit sufficient light to produce the required assay performance. Generally, the maximum power output of the laser diode should be from approximately 1 milliWatt (mW) to 1 Watt, preferably from 30 mW to 200 mW.

The light is carried to and from the well by fiber bundles. Any fiber bundle that transmits light at the wavelength of interest can be used in connection with this invention. However, the preferred fiber bundles are bundles consisting of fused silica multimode fibers, having diameters between 50 and 500 micrometers.

The filter used to eliminate extraneous light, including that which corresponds to the excitation wavelength band, can be any narrow or broad, optical filter capable of transmitting light in the emission wavelength band of interest and blocking light in the out-band emission wavelength region. The preferred filters are interference filters or colored-glass filters.

The light bundles are combined at the end facing the well in a configuration that allows the emitted light to be collected efficiently, and transmitted to the detector. Preferably, the fibers transmitting the excitation light are in the center of the end section, and occupy a low percentage of the overall bundle diameter. Generally, the ratio of the cross-sectional area of fibers transmitting light from the excitation light source, to the cross-sectional area of fibers transmitting light to the detector, is in the approximate range from 0.01 to 50 percent, preferably from 1 to 10%.

Figure 2:
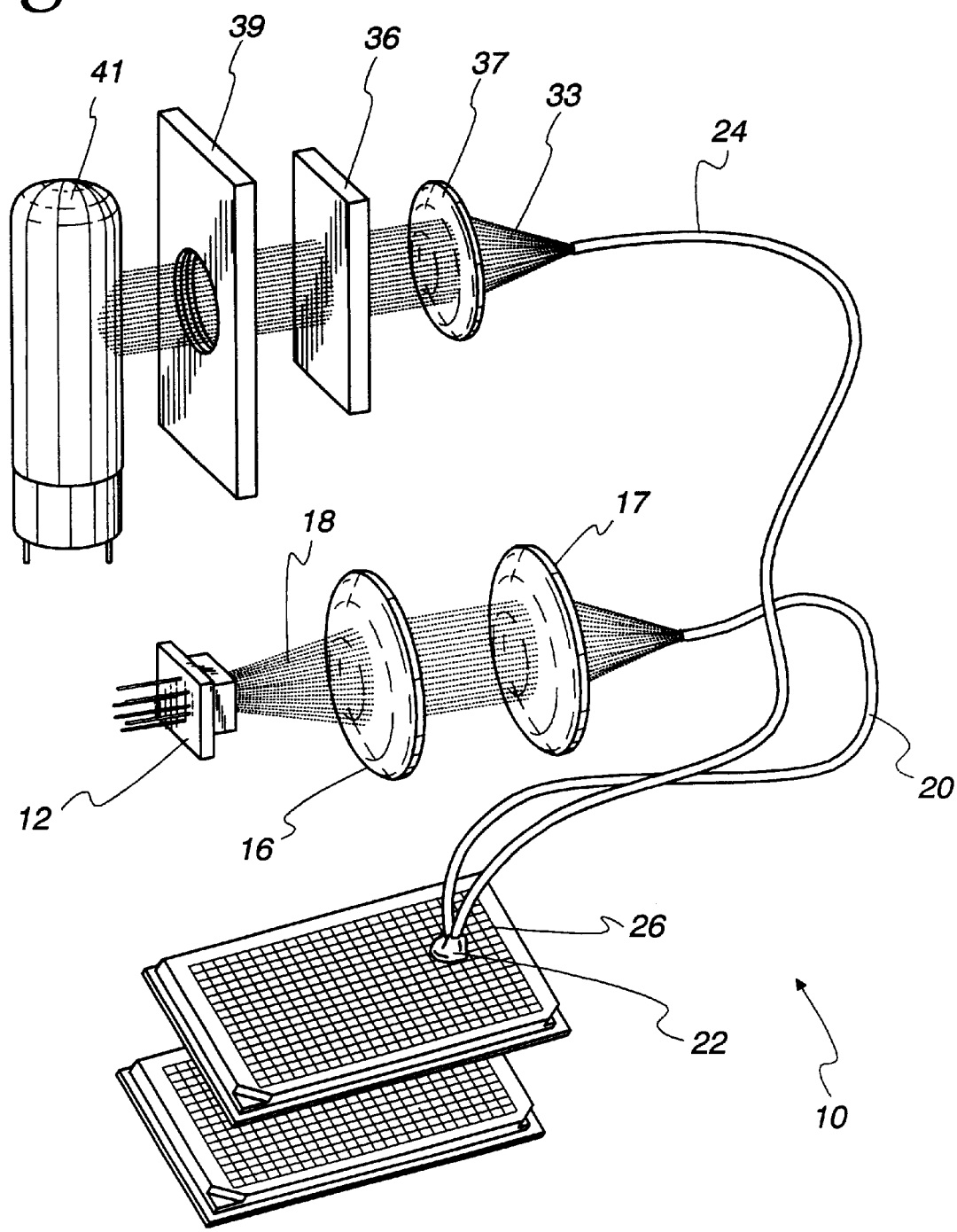
FIG. 2 is a perspective schematic view of the apparatus of FIG. 1, showing the location of selected components and of microplates having a plurality of wells.

The preferred embodiment of the present invention is shown in the accompanying drawings. FIGS. 1 and 2 display an analyzer, designated by the numeral 10, which is constructed in accordance with the present invention. The analyzer 10 includes a laser diode 12 and a lens compartment 14 containing two lenses. The currently preferred laser diode is CQL806/30 diode marketed by Philips. This diode emits light at 675 nm at a maximum optical output power of 30 mW. The CQL802/D diode marketed by Philips produces three times higher signal levels; however, the cost of this device is also three times higher compared to other commonly used diodes. Thus, it is preferred only for applications where the CQL806/30 diode does not provide sufficient optical illumination power for the desired assay performance. The two lenses are not shown in FIG. 1 but are shown in FIG. 2 and are designated by numerals 16 and 17. As shown schematically in FIG. 2, light 18 emitted by the laser diode 12, is directed by the lenses 16 and 17 into a fiber bundle 20. Currently, preferred fiber bundles consist of individual multimode fibers made of fused silica with a numerical aperture of 0.22 to 0.4. The total diameter of the currently preferred bundle is approximately 3 mm at the sample end. Coaxial fiber arrangement at the common end is preferred, especially for 1536-well plates, because the light at the excitation wavelength could be dispersed over adjacent wells in the microplate. As shown in FIGS. 1 and 2, the fiber bundle 20 extends from the lens compartment 14 to a well of a microplate 22. Currently preferred are microplates having either 96, 384 or 1536 wells. The fiber bundle 20 is joined with the fiber bundle 24 to form a bifurcated bundle 26.

Figure 3:
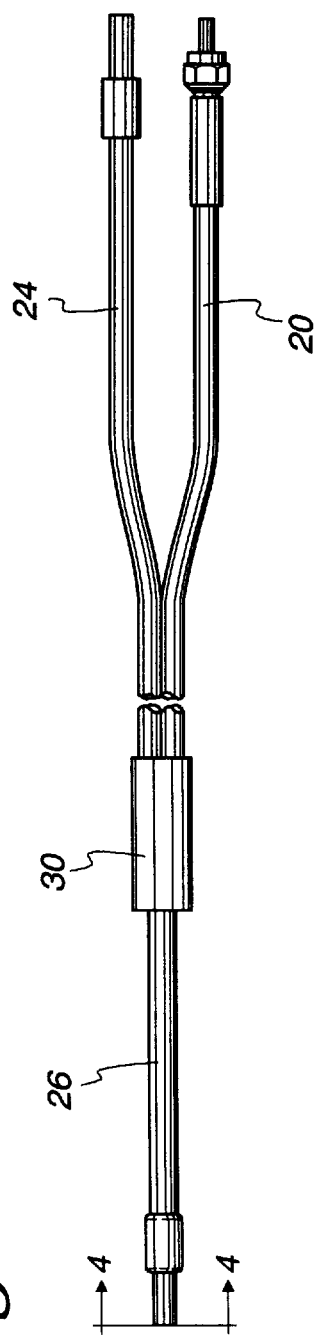
FIG. 3 is a side-elevational view of a co-axial light guide of the apparatus of FIG. 1.
Figure 4:
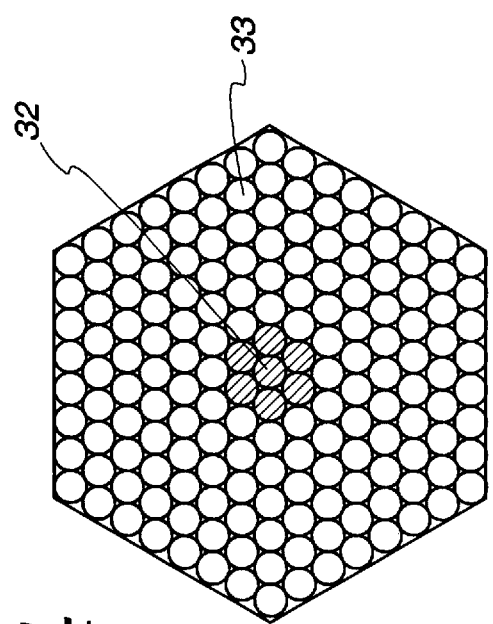
FIG. 4 is a cross-sectional view of the light guide of FIG. 3 taken along line 4—4 of FIG. 3.

To improve light collection efficiency and reduce crosstalk between wells in a microplate, a lens (not shown) is mounted at the sample end of the bifurcated bundle 26. The lens collimates the light emerging from the excitation fibers and directs it into the sample well. The lens defines the field of view in the well by its clear aperture and its numerical aperture. This is needed to mask the effective area from which the emitted light is collected to a size suitable for wells with different diameters. A lens having about a 3 mm diameter is preferred for 1536-well microplates, while larger clear-aperture lenses are preferred for lower density microplates, such as 384-well microplates. The use of high-numerical aperture lenses is preferred since more light emerging from the sample well can be collected. A typical numerical aperture shall be 0.5. The lens should be placed between 0.25 mm and 2 mm above the microplates. The preferred distance is 1 mm. The construction of the fiber bundles 20, 24 and 26 is shown in FIGS. 3 and 4. As displayed in FIG. 3, fiber bundles 20 and 24 are joined by a transition piece 30. As shown in FIG. 4, the bifurcated fiber bundle 26 has 169 fibers. Seven of these fibers, which are darkened and designated by a numeral 32, are the excitation fibers. One hundred sixty-two of the fibers located around the excitation fibers are the emission fibers, denoted by 33. The light carried by the fiber bundle 20 enters into the fiber bundles 32. The light then enters the medium of the well and the emitted light is collected by the fibers 33. The emitted light is carried by fibers 33 into the fiber bundle 24. As shown in FIGS. 1 and 2, the fiber bundle 24 transmits emitted light to the emission assembly 35. As shown schematically in FIG. 2, the emission assembly 35 includes a lens 37, which collimates the light collected from the fiber bundle 24 and directs it into an emission band-pass filter 36. Since the laser diode emits a large amount of light at 680 nm, the emission filters must effectively block this light to prevent damage to the photomultiplier tube if no shutter is used. At the present time, the custom 570DF100 filter manufactured by Omega Optical, Inc., is preferred. The emission band-pass filter 36 transmits light in the 520–620 nm wavelength range through a mechanical shutter 39 into a photomultiplier module 41. The currently preferred photomultiplier module is H6240-01, including a photomultiplier tube that has increased sensitivity in the emission wavelength of interest. This module is marketed by Hamamatsu Photonics.

The hardware and user interfaces are controlled by an in-house developed software package, which includes full instrument control, assay definition, sample mapping, data storage and reporting, and database management.

Figure 5:
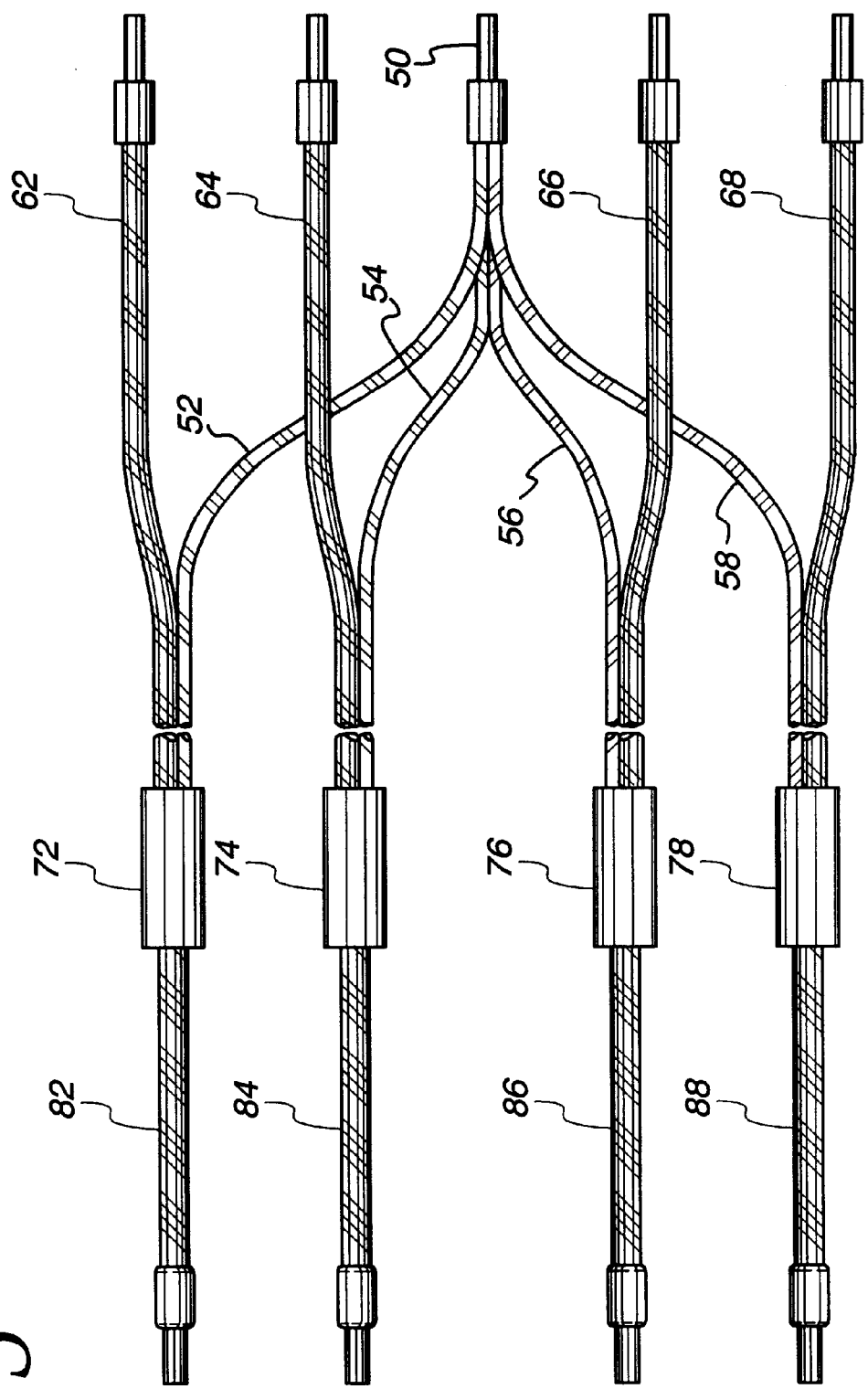
FIG. 5 is a side-elevational view of a light guide for 4 readhead fibers.

Another embodiment of the fiber bundle for use in the analyzer of the present invention is shown in FIG. 5. The fiber bundle 50 shown in FIG. 5 collects light emitted from a single laser diode (not shown) and directs the light to four fiber bundles 52, 54, 56 and 58. The fiber bundles 52, 54, 56 and 58 which are joined with corresponding emission fiber bundles 62, 64, 66 and 68 in the same manner as the fiber bundles shown in FIG. 3 to produce the cross-sectional view as shown in FIG. 4. FIG. 5 shows an example of having one common light source for measuring four samples in four different wells simultaneously by means of four emission assemblies. Other numbers of light sources and detectors per channel are possible. In particular, the combination of having one light source illuminating multiple wells, and one (multi-channel) detector to detect the emission light of multiple wells can be implemented.

EXAMPLES

The following examples are provided to further illustrate the present invention. They are not intended to limit the present invention in any manner.

Example 1

Enzyme Assay (Tyrosine Kinase)

Figure 6:
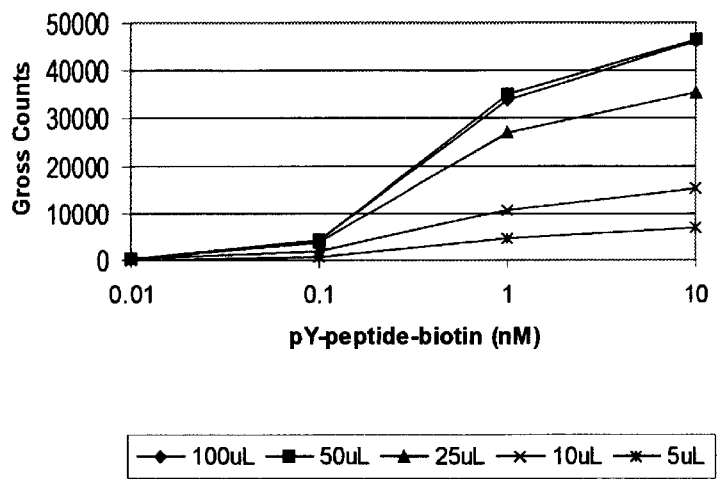
FIG. 6 is a graph showing the results of a Tyrosine Kinase LOCI Sandwich Assay.

In this example, an antiphosphotyrosine antibody is conjugated to the LOCI Chemiluminescer bead. Streptavidin is conjugated to the LOCI Sensitizer bead. Biotinylated phosphotyrosine peptide is diluted in assay buffer to known concentrations. Appropriate volumes of each component are added to wells of a microplate, mixed, and incubated. The microplate is then loaded into the measurement apparatus and the light emitted by each well is measured. The light intensity is proportional to the concentration of the biotinylated phosphotyrosine peptide. FIG. 6 depicts typical results for a range of sample volumes.

Other experiments have demonstrated a sensitivity of 125 femtograms of the phosphotyrosine peptide in as little as 60 nL in a labchip, wherein reagents are dispensed, mixed, incubated, and analyzed in an integrated miniaturized disposable device.

Example 2

Protein-Protein Assay (GST-Girk)

Figure 7:
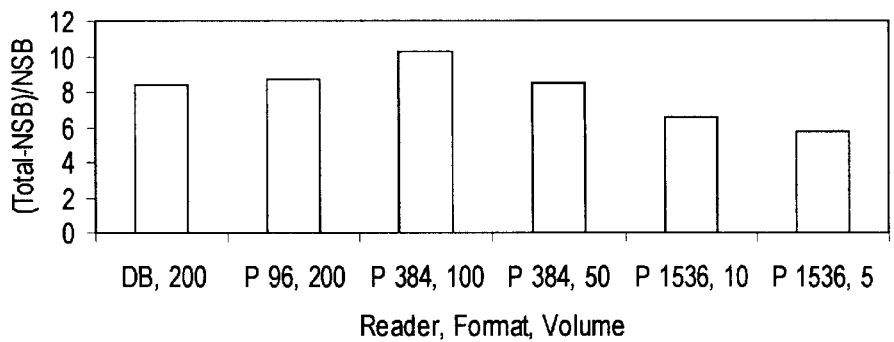
FIG. 7 is a graph depicting GST—Girk Assay Signal to Noise.

In this example, an anti-GST antibody is conjugated to the LOCI Chemiluminescer bead. Streptavidin is conjugated to the LOCI Sensitizer bead. Biotinylated GBγ protein is diluted in assay buffer to a known concentration. Appropriate volumes of each component are added to wells of a microplate, mixed, and incubated. The microplate is then loaded into the measurement apparatus and the light emitted by each well is measured. The light intensity is proportional to the concentration of the biotinylated GBγ protein. FIG. 7 depicts typical Signal to Blank ratios for a range of sample volumes and microplate formats.

Example 3

Receptor Binding Assay (TNF-α)

Figure 8:
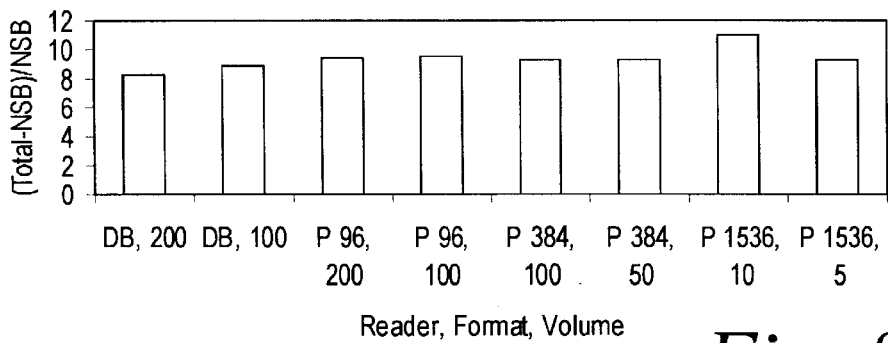
FIG. 8 is a graph depicting TNF—a Assay Signal to Noise.

In this example, an anti-TNFαRI antibody is conjugated to the LOCI Chemiluminescer bead. Streptavidin is conjugated to the LOCI Sensitizer bead. Biotinylated TNFα and TNFαRI receptor are diluted in assay buffer to known concentrations. Appropriate volumes of each component are added to wells of a microplate, mixed, and incubated. The microplate is then loaded into the measurement apparatus and the light emitted by each well is measured. The light intensity is proportional to the concentration of the biotinylated TNFαRI FIG. 8 depicts typical Signal to Blank ratios for a range of sample volumes and microplate formats.

We claim:

1. A photochemical method for measuring light emitted by a liquid subjected to an excitation light said liquid contained in a vessel, said method comprising:

(a) producing an excitation light having a first wavelength band, for a pre-determined time period;

(b) transmitting said excitation light into said liquid through a fiber bundle;

(c) said liquid producing, in a photochemical response to said excitation light, an emitted light having a second wavelength band, said second wavelength band being shorter than and separated from said first wavelength band;

(d) passing said emitted light to a detector through a fiber bundle surrounding and coaxial with the fiber bundle of (a);

(e) detecting said emitted light for a predetermined period of time after producing of said excitation light ceases;

(f) determining the amount of light received by said detector, said amount being indicative of the amount of said emitted light produced by said liquid; and, (g) shielding said detector from said excitation light when said excitation light is being produced.

2. The method of claim 1 further comprising the step of passing said emitted light through a filter to exclude at least the light at said first wavelength band, before step (d).

3. The method of claim 2 wherein the emitted light passing through the filter has wavelengths in the range from about 500 nanometers to about 650 nanometers.

4. The method of claim 2 wherein the emitted light passing through the filter has wavelengths in the range from about 520 nanometers to about 620 nanometers.

5. The method of claim 1 wherein said excitation light has an intensity in the range from about 1 milliWatt to about 1 Watt.

6. The method of claim 1 wherein said excitation light has an intensity in the range from about 30 milliWatts to 200 milliWatts.

7. The method of claim 1 wherein said excitation light has an intensity of about 100 milli Watts.

8. The method of claim 1 wherein said excitation light is produced by a laser diode, a gas laser, a solid state laser, a light emitting diode or a white light lamp.

9. The method of claim 1 wherein said excitation light is produced by a laser diode.

10. The method of claim 1 wherein said excitation light is produced by a flash lamp.

11. The method of claim 1 wherein said excitation light is produced by a white light lamp.

12. The method of claim 1 wherein said excitation light is produced by a Xenon flash lamp.

13. The method of claim 1 wherein said first wavelength band has a first median wavelength and said second wavelength band has a second median wavelength and wherein said first median wavelength is longer than said second median wavelength.

14. The method of claim 1 wherein the first wavelength band is in a range from about 670 nanometers and 690 nanometers.

15. The method of claim 1 further comprising repeating steps (a) through (g) a predetermined number of times or for a predetermined time for the same liquid in the same vessel and determining a composite amount of light received by said detector.

16. The method of claim 1 wherein said fiber bundles comprise a bifurcated fiber bundle having a common end facing said liquid, a first fiber bundle in the center of said bundle for transmitting said excitation light, and a second fiber bundle surrounding and coaxial with said first fiber bundle for passing said emitted light.

17. The method of claim 16 wherein the ratio of the excitation fiber bundles to the emission fiber bundles is in the range from about 0.01 to about 0.1.

18. The method of claim 16 wherein the ratio of the excitation fiber bundles to the emission fiber bundles is in the range from about 0.02 to about 0.06.

19. The method of claim 1 wherein said emitted light is produced by chemiluminescence.

20. The method of claim 1 wherein said emitted light is produced by an interaction between donor and acceptor particles in said liquid.

21. The method of claim 20 wherein said donor and acceptor particles are for conducting luminescence oxygen channeling immunoassays.

22. The method of claim 1 wherein the step of shielding is carried out by using a shutter.

23. The method of claim 22 wherein the light shutter is a mechanical device, an electronic device or a photomultiplier tube-gating device.

24. The method of claim 1 wherein the detector is a photomultiplier tube, an avalanche photodiode, a charge coupled device or a silicon photodiode.

25. The method of claim 1 wherein the detector is a photomultiplier tube.

26. The method of claim 1 wherein the detector is a charge coupled device array.

27. The method of claim 1 wherein the excitation light is produced at a stable energy level and at a stable wavelength.

28. The method of claim 1 wherein the volume of said liquid is in the range from about 0.01 to microliters about 300 microliters.

29. The method of claim 1 wherein the volume of said liquid is in the range from about 1 microliter to about 100 microliters.

30. The method of claim 1 wherein said vessel is an opaque microplate well or a single channel of a lab chip containing multiple channels.

31. The method of claim 1 wherein said vessel is a white microplate well.

32. The method of claim 1 wherein steps (a) through (g) are carried out simultaneously in a plurality of vessels.

33. The method of claim 32 wherein steps (a) through (g) are carried out simultaneously in a plurality of vessels of a microplate.

34. The method of claim 33 wherein a single detector collects light emitted from a plurality of vessels.

35. The method of claim 33 wherein the excitation light from a single source is transmitted to a plurality of vessels.

36. An optical measurement system for producing excitation light and measuring light emitted by a sample by a photochemical reaction in a vessel, said system comprising:
- a light source, said light source producing light in an excitation wavelength band;
- a first fiber bundle for transmitting the light to liquid in said vessel;
- a second fiber bundle for transmitting the light emitted from said well, said light being emitted at an emitted wavelength shorter than and separated from said excitation wavelength;
- a filter, said filter reducing light at an excitation wavelength band and passing at least a portion of the emitted light;
- a detector, said detector receiving said emitted light and determining the amount of said emitted light;
- a shutter; and
- a controller for closing said shutter whenever said light source is producing said excitation light.

37. The system of claim 36 wherein the first fiber bundle and the second fiber bundle are joined to produce an end section having parallel first fiber bundle fibers and second fiber bundle fibers, in which the second fiber bundle fibers surround and are coaxial with the first fiber bundle fibers.

38. The system of claim 37 wherein the ratio of cross-sectional areas of the first fiber bundle to the second fiber bundle is in the range from about 0.01 to about 0.1.

39. The system of claim 37 wherein said ratio is in the range from about 0.02 to about 0.06.

40. The system of claim 36 wherein the light source produces light having an intensity in the range from about 1 milliWatt to about 1 Watt.

41. The system of claim 36 wherein the light source produces light having an intensity in the range from about 30 milliWatts to about 200 milliWatts.

42. The system of claim 36 wherein the light source produces light having an intensity about 100 milliWatts.

43. The system of claim 36 wherein the light source is a laser diode, a gas laser, a solid state laser, a light emitting diode or a white light lamp.

44. The system of claim 36 wherein the light source is a laser diode.

45. The system of claim 36 wherein the light source is a flash lamp.

46. The system of claim 36 wherein the light source is a Xenon flash lamp.

47. The system of claim 36 wherein the detector is a photomultiplier tube, an avalanche photodiode, a charge coupled device or a silicon photodiode.

48. The system of claim 36 wherein the detector is a photomultiplier tube.

49. The system of claim 36 wherein the excitation wavelength band extends from about 670 nanometers to about 690 nanometers.

50. The system of claim 36 wherein the filter passes light in the wavelength band from about 500 nanometers to about 650 nanometers.

51. The system of claim 36 wherein the filter passes light in the wavelength band from about 520 nanometers to about 620 nanometers.

52. The system of claim 36 wherein the shutter is a mechanical device, an electronic device or a photomultiplier tube-gating device.

53. The system of claim 36 wherein the volume of said liquid is in the range from about 1 microliter to about 100 microliters.

54. The system of claim 36 wherein said vessel is an opaque well of a microplate or a singlechannel of a lab chip containing multiple channels.

55. The system of claim 36 wherein said vessel is a white microplate well.

56. The system of claim 36 further comprising a plurality of said first and second fiber bundles for carrying said excited light to a plurality of vessels.

57. The system of claim 36 wherein the volume of said liquid is in the range from about 0.01 to about 300 microliters.

58. The system of claim 36 further comprising at least one lens between said second fiber bundle and said detector.

59. The system of claim 36 further comprising at least one lens between said light source and said first fiber bundle.

60. The system of claim 36 further comprising at least one lens between said liquid and said end section.

61. The method of claim 1 wherein the ratio of the excitation time of (a) to the detecting time of (e) is between 0.1 and 0.5.

62. The method of claim 61 wherein the ratio of excitation time to detecting time is about 0.3.

* * * * *